United States Patent
Karkanias et al.

(10) Patent No.: US 8,260,272 B2
(45) Date of Patent: *Sep. 4, 2012

(54) HEALTH-RELATED OPPORTUNISTIC NETWORKING

(75) Inventors: Chris Demetrios Karkanias, Sammamish, WA (US); Stephen Edward Hodges, Cambridge (GB); James William Scott, Cambridge (GB)

(73) Assignee: Microsoft Corporation, Redmond, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/224,171

(22) Filed: Sep. 1, 2011

(65) Prior Publication Data
US 2011/0320564 A1 Dec. 29, 2011

Related U.S. Application Data

(63) Continuation of application No. 11/680,073, filed on Feb. 28, 2007, now Pat. No. 8,032,124.

(51) Int. Cl.
*H04M 3/42* (2006.01)

(52) U.S. Cl. ............... 455/414.1; 455/41.2; 455/502; 370/238

(58) Field of Classification Search ........... 455/414.1, 455/502, 41.2; 370/238, 338, 260
See application file for complete search history.

(56) References Cited

U.S. PATENT DOCUMENTS

| | | | |
|---|---|---|---|
| 6,199,099 B1 | 3/2001 | Gershman et al. | |
| 6,282,577 B1 | 8/2001 | Okanoue et al. | |
| 6,421,232 B2 | 7/2002 | Sallam | |
| 6,516,316 B1 | 2/2003 | Ramasubramani et al. | |
| 6,816,882 B1 | 11/2004 | Conner et al. | |
| 6,822,639 B1* | 11/2004 | Silverbrook et al. | 345/173 |
| 6,850,502 B1 | 2/2005 | Kagan et al. | |
| 6,965,568 B1* | 11/2005 | Larsen | 370/238 |
| 6,980,537 B1 | 12/2005 | Liu | |
| 6,988,056 B2 | 1/2006 | Cook | |
| 7,072,650 B2 | 7/2006 | Stanforth | |
| 7,099,297 B2 | 8/2006 | Hughes et al. | |

(Continued)

FOREIGN PATENT DOCUMENTS

KR   1020010013499 A   2/2001

(Continued)

OTHER PUBLICATIONS

Raffaele Bruno, et al. Mesh Networks: Commodity Multihop Ad Hoc Networks. http://bruno1.iit.cnr.it/~bruno/files/commag05.pdf. pp. 123-131. Last accessed Nov. 30, 2006.

(Continued)

*Primary Examiner* — Anthony Addy
*Assistant Examiner* — Shahriar Behnamian
(74) *Attorney, Agent, or Firm* — Hope Baldauff Hartman, LLC

(57) ABSTRACT

A wireless opportunistic network that can facilitate data transfer by way of interconnected devices is disclosed. In accordance with this opportunistic network, each of the devices effectively contributes to the transfer of the information thereby obviating the need for an external carrier. In this manner, the carrier infrastructure is embodied and distributed throughout the individual devices of the network. In a particular aspect, the opportunistic network is employed to transfer and make available health-related data. This functionality can be used in many scenarios related to heath from, monitoring patients and conveying basic diagnostic data to identifying bioterrorism by way of collaborating data between a number of devices within the network. Essentially, the innovation provides for at least two core functional ideas, the opportunistic network infrastructure and the use of the network in health related scenarios.

20 Claims, 15 Drawing Sheets

U.S. PATENT DOCUMENTS

| | | | |
|---|---|---|---|
| 2002/0032751 | A1 | 3/2002 | Bharadwaj |
| 2002/0087674 | A1 | 7/2002 | Guilford et al. |
| 2002/0104011 | A1 | 8/2002 | Svoboda et al. |
| 2003/0065715 | A1 | 4/2003 | Burdick et al. |
| 2003/0179742 | A1 | 9/2003 | Ogier et al. |
| 2004/0097260 | A1 | 5/2004 | Stenton et al. |
| 2005/0037787 | A1 | 2/2005 | Bachner et al. |
| 2005/0102377 | A1 | 5/2005 | King et al. |
| 2005/0117527 | A1 | 6/2005 | Williams et al. |
| 2005/0153725 | A1 | 7/2005 | Naghian et al. |
| 2005/0181734 | A1 | 8/2005 | Coutts et al. |
| 2005/0185606 | A1 | 8/2005 | Rayment et al. |
| 2006/0166740 | A1 | 7/2006 | Sufuentes |
| 2006/0198448 | A1 | 9/2006 | Aissi et al. |
| 2007/0050522 | A1 | 3/2007 | Grove et al. |
| 2007/0133665 | A1 | 6/2007 | Litwin |
| 2007/0197881 | A1 | 8/2007 | Wolf et al. |

FOREIGN PATENT DOCUMENTS

| | | |
|---|---|---|
| WO | WO 98/56140 | 10/1998 |
| WO | WO0025485 | 5/2000 |
| WO | 2004088874 A2 | 10/2004 |

OTHER PUBLICATIONS

Imrich Chlamtack, et al. Mobile ad hoc networking: imperatives and challenges. http://www.ece.ncsu.edu/wireless/Resources/Papers/adhocSurvey.pdf. pp. 13-64. Last accessed Nov. 30, 2006.

Miklos Aurel Ronai, et al. A Simple Neighbour Discovery Procedure for Bluetooth Ad Hoc Networks. http://www.ronai.hu/doc/GlobeCom2003-NDP_for_Bt.pdf. Last accessed Nov. 30, 2006.

OA dated Jan. 27, 2010 for U.S. Appl. No. 11/680,073, 35 pages.

International Search Report for PCT Patent Application No. US2008/053546 dated Jun. 25, 2008; 3 pages.

OA dated Jul. 26, 2010 for U.S. Appl. No. 11/680,073, 29 pages.

OA dated Dec. 9, 2010 for U.S. Appl. No. 11/680,073, 26 pages.

U.S. Notice of Allowance dated May 27, 2011 in U.S. Appl. No. 11/680,073.

U.S. Official Action dated Apr. 29, 2010 in U.S. Appl. No. 11/754,528.

U.S. Official Action dated Oct. 15, 2010 in U.S. Appl. No. 11/754,528.

U.S. Official Action dated Mar. 28, 2011 in U.S. Appl. No. 11/754,528.

U.S. Official Action dated Oct. 6, 2011 in U.S. Appl. No. 11/754,528.

U.S. Official Action dated Feb. 21, 2012 in U.S. Appl. No. 11/754,528.

Landis et al., "Reaching out to the Cell Phone with Jini," 2002, Proceedings of the 35th Hawaii International Conference on System Sciences, 10 pp.

Stajano et al., "The Thinnest of Clients: Controlling It All Via Cellphone," 1998, Mobile Computing and Communications Review, vol. 2(4), 8 pp.

Sundelof, "Are Cell phones the Thin Client of the World Wide Web or a Part of the World Wide Web?" Dec. 2006, http://inthefieldonline.netlinthefieldonline_w3c_bangalore_dec2006.pdf. Last accessed Nov. 20, 2006. 6 pp.

* cited by examiner

HEALTH-RELATED OPPORTUNISTIC NETWORKING

CROSS-REFERENCE TO RELATED APPLICATION

This application is a continuation of U.S. patent application Ser. No. 11/680,073 filed on Feb. 28, 2007 and entitled "HEALTH-RELATED OPPORTUNISTIC NETWORKING," the entire contents of which are incorporated herein by reference.

BACKGROUND

With the ever-increasing popularity of personal mobile devices, e.g., cell phones, smartphones, personal digital assistants (PDAs), personal music players, laptops, etc., 'mobility' has been the focus of many consumer products as well as services of wireless providers. For example, in the telecommunications industry, 'mobility' is at the forefront as consumers are no longer restricted by location with regard to communications and computing needs. Rather, today, as technology advances, more and more consumers use portable devices in day-to-day activities, planning and entertainment.

As mobile device popularity increases, the ability to make telephone calls, access electronic mail, communicate via instant message (IM) and access online services from any location has also continued to evolve. Although wireless technology for data transmission has been available for quite some time, limitations such as bandwidth and area coverage plague service providers. More particularly, these types of limitations have prevented providers from seamlessly establishing mass deployments of wireless networks.

More recent innovations such as the WiFi standards and other expanded wireless technologies have made it possible to deploy location-based (e.g., city-wide) wireless access networks and thereafter, to offer revenue-generating mobile wireless access services. However, most often, these wireless access networks do not extend to less populated areas due to driving economic concerns. Rather, these conventional networks target areas with a high population density and do not address those potential consumers in less populated areas. This lack of expansion is most often due to the wired characteristics of the wireless repeater nodes, as well as costs associated therewith. For example, most often, rural areas are not covered by the service area of a conventional cell tower or mesh network thereby leaving a gap in the coverage area.

An 'opportunistic' network can refer to the use of a co-operating set of mobile or stationary devices to transfer data whenever connection opportunities arrive. These opportunities may be limited by the effects of mobility, bandwidth limitations, and other factors. Both wired and wireless links can be used as connection opportunities. Opportunistic networks have the advantage of being able to employ "store and forward" data transfer where data is not sent from one end of the network to the other immediately, but is instead passed hop-by-hop and stored on intermediate nodes until that node has a suitable connection opportunity to pass it on in turn. This allows opportunistic networks to cope with large variations in network topology and with poor link qualities, in addition to traditional networking situations (e.g. where Internet access is available).

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises an opportunistic network that can facilitate data transfer through a group of network connected devices where each device effectively contributes to the transfer of the information. In other words, the innovation describes an opportunistic network of devices where an external carrier need not be used in order to transfer data. Rather, the carrier infrastructure is embodied and distributed throughout the individual devices comprising the network.

In one aspect, the innovation describes a store/forward model by way of the opportunistic network whereby health-related data can be communicated to and shared between devices. This sophisticated communication framework can be based upon a peer-to-peer (P2P) framework, or combination of P2P together with an external (e.g., cell tower) infrastructure. For example, the infrastructure can be a completely ad hoc P2P or combination of ad hoc together with a traditional hub-and-spoke framework.

In various health-related aspects, the innovation can be applied to situations ranging from monitoring basic health-related patient criteria to proactively identifying and alerting of natural disasters and/or bioterrorism. In other words, if an effect is observed, it can be reported, captured and subsequently transferred across the opportunistic network to ensure prompt attention to the matter.

In yet another aspect thereof, a machine learning and reasoning (MLR) component is provided that employs a probabilistic and/or statistical-based analysis to prognose or infer an action that a user desires to be automatically performed. By way of example, MLR mechanisms can be employed to make inferences that facilitate timely and accurate transmission of data across the network, and to infer the correct recipient depending on properties of the data itself. In a specific example, an MLR component, based upon type of data, time of day and other contextual factors, can determine which devices to select as the destination for the data, and also as carriers across the opportunistic network in order to ensure timely and safe delivery of the data.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
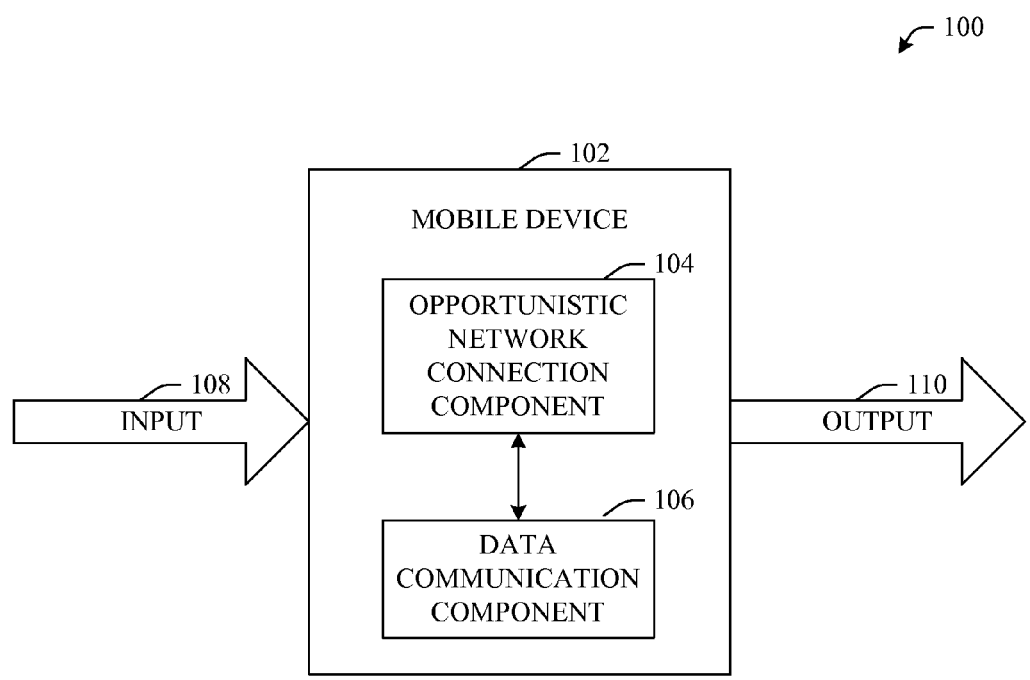
FIG. 1 illustrates a mobile device that facilitates transmission of data across an opportunistic network in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring initially to the drawings, FIG. 1 illustrates a system 100 that facilitates transmission of data across an opportunistic network in accordance with an aspect of the innovation. Generally, system 100 illustrates a mobile device 102 having an opportunistic connection component 104 and a data communication component 106 therein. These components (104, 106) enable the transfer of an input (e.g., 108) to a target device (not shown). In other words, output (e.g., 110) can be delivered to a target device from mobile device 102 without any external infrastructure.

As will be understood upon a review of the figures that follow, the communication infrastructure can be totally encapsulated within network-connected mobile devices (e.g., 102) in the form of an opportunistic connection component 104 and a data communication component 106. In other words, in one example, a peer-to-peer (P2P) type infrastructure can be established such that the external communication infrastructures are not necessary to enable communication. However, it is to be understood that some of the features, functions and benefits described herein can be employed in other, more conventional, infrastructures such as hub and spoke (e.g., cell tower-based) infrastructures as well as combinations with P2P infrastructures.

Figure 2:
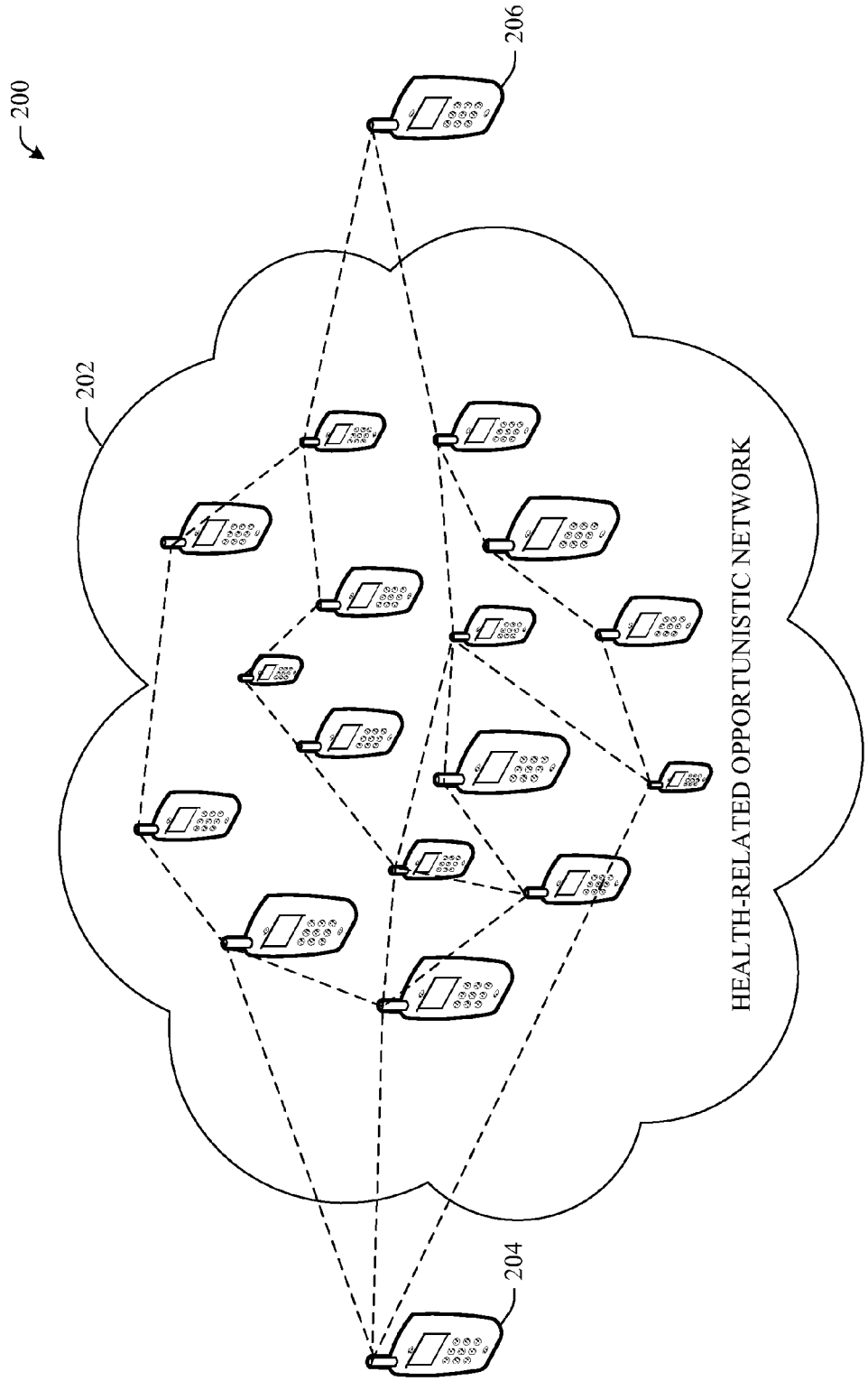
FIG. 2 illustrates an example wireless opportunistic network in accordance with an aspect of the innovation.

Referring now to FIG. 2, there is illustrated a system 200 that facilitates the transmission of health-related data by way of an opportunistic network. As shown, a health-related opportunistic network 202 can be employed to transfer data between an origin device 204 to a target device 206. Because mobile devices (e.g., cell phones) are ubiquitous in many markets today, it can be possible to establish a peering network or opportunistic network 202 such that each device can participate in information transfer throughout the network. As depicted by dashed lines throughout the network 202, information can have multiple paths by which it can travel from an origin device 204 to a target device 206. These multiple paths illustrate sophisticated collaboration between the devices with respect to bandwidth, available processing capacity, signal strength, cost, security, etc. Effectively, logic within each device can establish redundancies associated with the type of data which can ensure timely and accurate delivery.

In summary, the subject innovation relates to an opportunistic network 202 that can be established between network-connected mobile devices (e.g., 204, 206), for example, cellular telephones, personal digital assistants (PDAs), smartphones or the like. Rather than employing conventional cell towers that provide a centralized topology, the innovation shifts to an 'erratic' or dynamic topology 202 where each mobile device can carry a piece of traffic such that the infrastructure is integral to the mobile device itself (or group of devices themselves). In one example, it is possible to use the opportunistic network 202 as an intranet where data packets can be aggregated and passed to devices within the network.

It will be appreciated that one feature/benefit of the opportunistic network 202 is that low communication signals can be mitigated and possibly eliminated. Reduction and/or elimination of low signal problems is essentially possible because the vast number of mobile (e.g., cellular) devices employed will effectively create a service grid 202 where each device is a node of the grid 202. As an inherent feature of the grid 202, each device can obtain service through a number of proximate devices. Thus, redundancy can be accomplished thereby enhancing performance of the system 200.

Overall, this opportunistic network 202 can provide ubiquitous connectivity and/or computing between network-connected devices. In other words, the more connected devices available, the better they can participate in the health-related eco-system of the subject innovation. As described supra, it is also to be understood that this 'opportunistic' 202 technique can be applied to most any type of portable and/or mobile computing device such as cellular telephones, smartphones, PDAs, laptops or the like.

In one particular aspect, the opportunistic network 202 can execute applications with particular networking needs in a health-care context. For example, a first device 204 such as an event recorder component can be used to capture images of events associated with a monitored entity (e.g., patient, elderly person). The images can be initially stored on the first device and transferred to a subsequent device when an opportunistic connection is able to be established. In other words, when the location of the origin device in relation to the opportunistic network 202, or in relation to at least one device of the opportunistic network, permits connectivity, the images can be automatically transferred in a P2P manner. As will be understood, this transfer can occur instantaneously (e.g., real-time), or stored/forwarded in accordance with forward criteria. For instance, images can be batch downloaded based upon a user-defined or location-based trigger.

Figure 3:
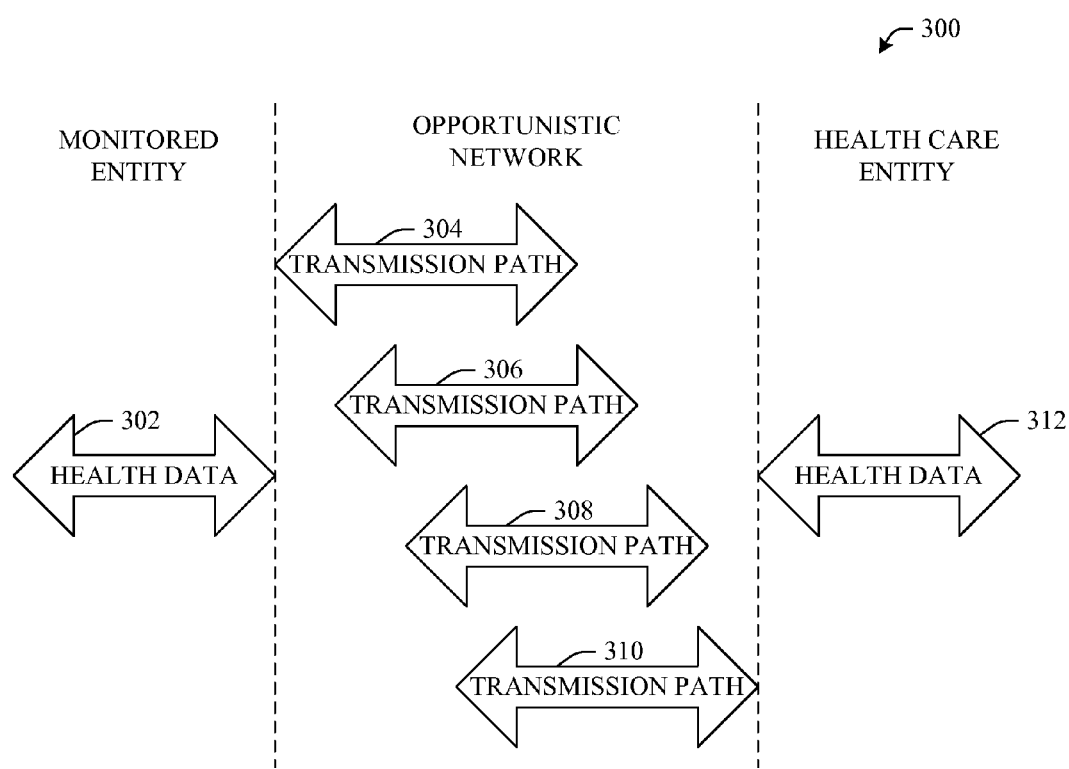
FIG. 3 illustrates an example data handoff by way of nodes of an opportunistic network in accordance with an aspect of the innovation.

FIG. 3 is provided to add perspective to an aspect of the innovation. Effectively, FIG. 3 illustrates an example data handoff 300 between devices of an opportunistic network. As shown, health data 302 can be transmitted from a monitored entity to a first device. This handoff of data is illustrated as a first transmission path 304. Subsequently, the data can be passed or forwarded to other devices within the opportunistic network as indicated by transmission paths 306-310. Although only four passes are illustrated in FIG. 3, it is to be appreciated that the opportunistic network can include N devices, where N is an integer.

Accordingly, the data can be passed throughout the opportunistic network until ultimately reaching the end device 312. It is to be understood and appreciated that this example illustrated in FIG. 3 is somewhat simplistic in nature and is provided to illustrate core concepts of store/forward of the innovation. In other aspects, multiple paths can be established between devices in order to effectively and/or efficiently transfer data within the opportunistic network. These alternative aspects are to be included within the scope of the innovation and claims appended hereto.

Figure 4:
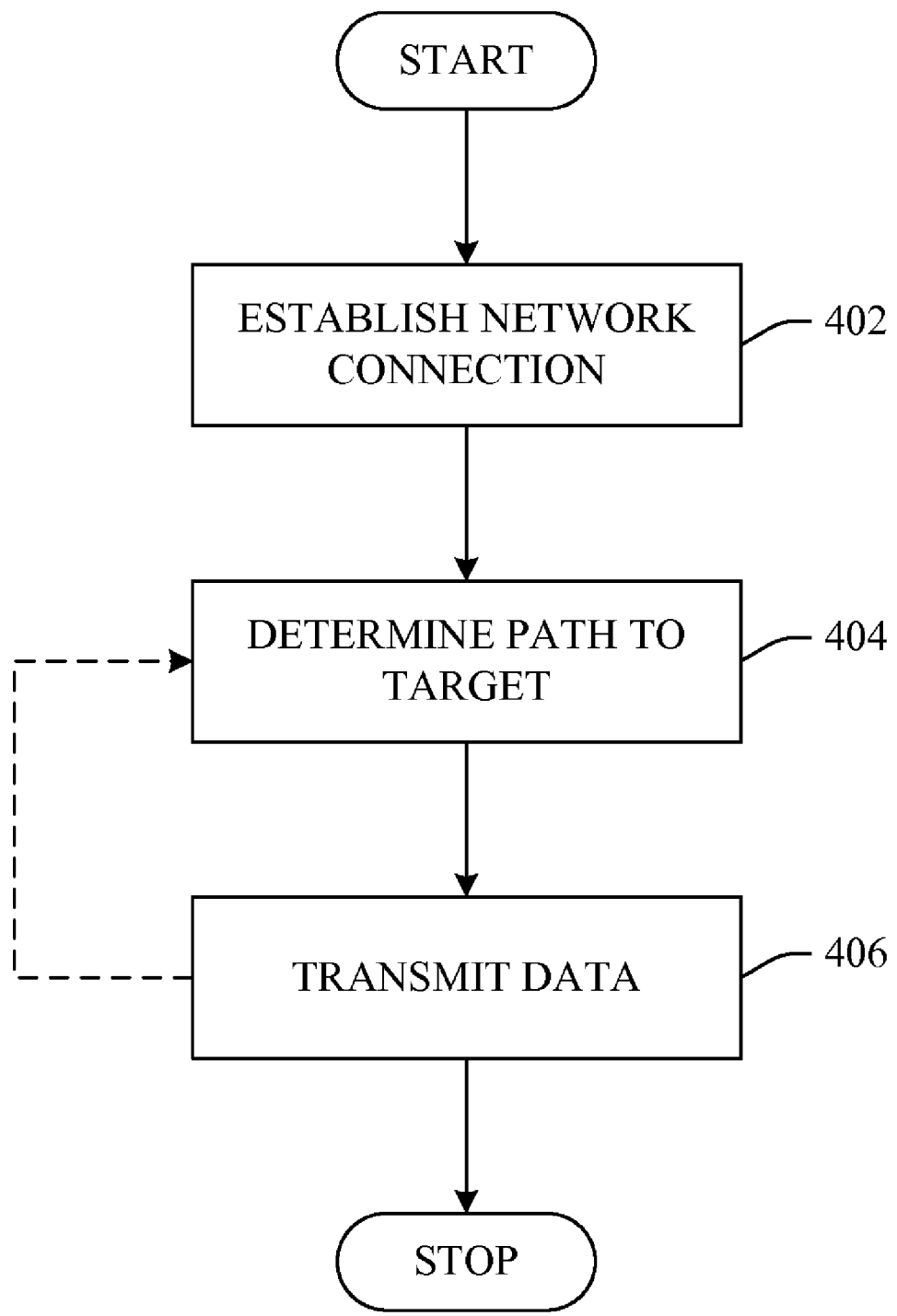
FIG. 4 illustrates an example flow chart of procedures that facilitate transfer of data across a network in accordance with an aspect of the innovation.

FIG. 4 illustrates a methodology of transmitting data within an opportunistic networking accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 402, an opportunistic connection can be established, for example, a P2P connection can be established directly between mobile devices (e.g., cell phones). In other aspects, 'hybrid' connections can be established, for example, a connection to a opportunistic network can be established that employs both P2P as well as conventional hub-and-spoke (e.g., cell tower) technologies. It is to be understood that the innovation described herein includes most any connection framework or infrastructure completely or partially embodied within a distributed mobile device network. As such, although many examples described herein are directed to a P2P protocol, other examples exist and are to be included within the scope of this disclosure and claims appended hereto.

A path from an origin device (or group of devices) to a target device (or group of devices) can be determined at 404. In other words, whether, one-to-many, many-to-many, many-to-one, or one-to-one, a path (or appropriate paths) throughout the network can be determined at 404. This path(s) can identify hops necessary to reach a desired target location as a function of most any criteria, including but not limited to, location, time of day, context, traffic content, sender identity, receiver identity, etc. As will be understood upon a review of the figures that follow, a policy and/or inference can be used to determine the path throughout the network.

Once a path is determined, the data can be transmitted at 406. However, it is to be understood that, in aspects, the complete path need not be determined before the data is transferred. Rather, only the next hop toward a target location needs to be established. For example, because the network can be dynamically changing (e.g., as mobile devices travel in/out of range), each hop within the journey to the target can be independently determined. This is indicated by the dashed line between 406 and 404, which effectively denotes the possible recursive nature of these acts within the methodology.

Figure 5:
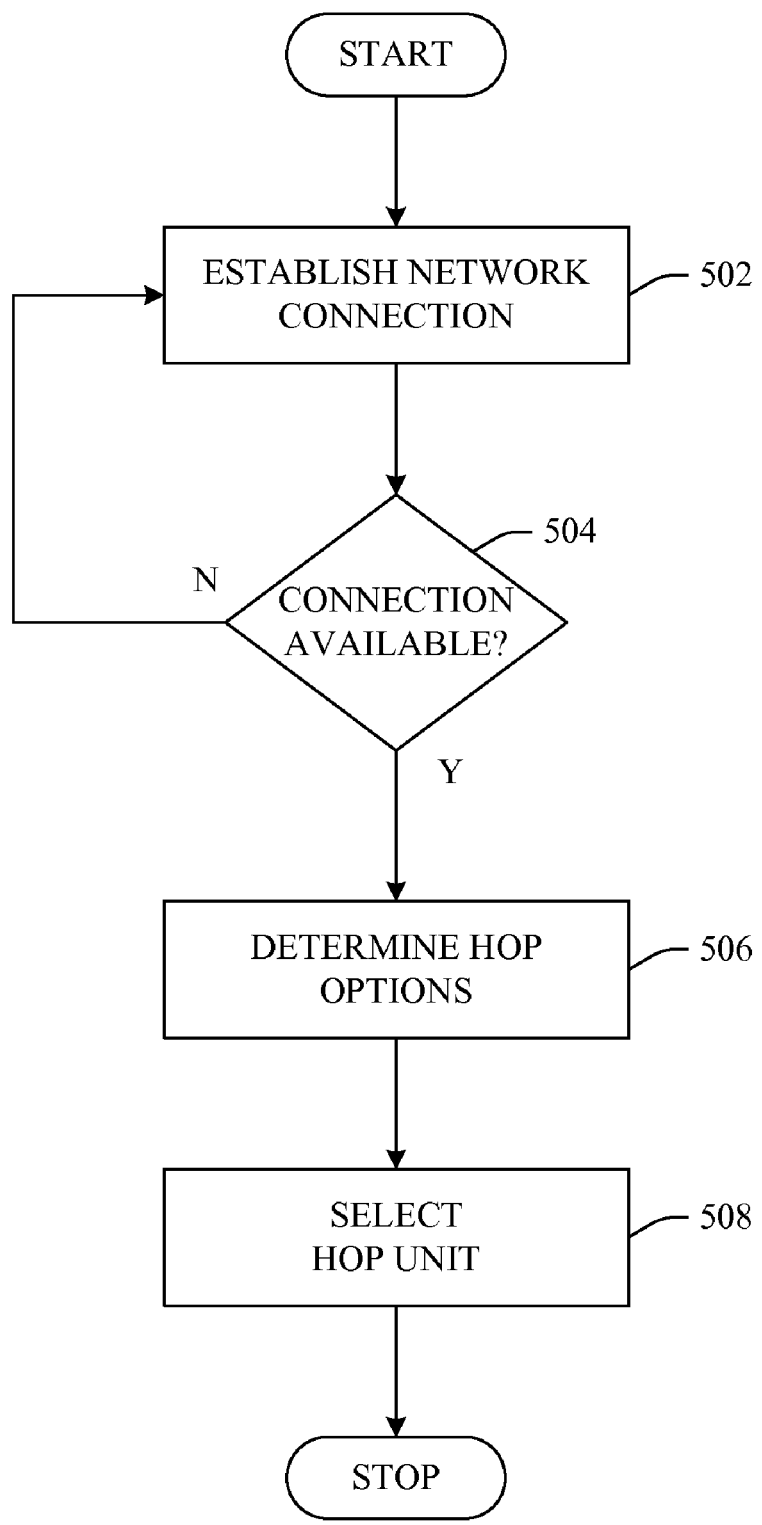
FIG. 5 illustrates an example flow chart of procedures that facilitate establishment of a hop or carrier path through an opportunistic network in accordance with an aspect of the innovation.

Referring now to FIG. 5, there is illustrated a methodology of establishing and selecting a connection in accordance with an aspect of the innovation. Essentially, this methodology illustrates the ability to employ sophisticated intelligence or logic as well as inference mechanisms to establish a connection within the opportunistic network by which data can be transmitted. Accordingly, a different connection can be selected for a routine voice call as would be for a priority health-related data transfer (e.g., life threatening heart rate).

Similarly, a different connection can be selected for unprivileged versus confidential or classified information. This connection can be a function of the number of hops necessary to reach a target, integrity of the carrier unit, etc. By way of further example, an analysis can be determined with regard fluidity of the opportunistic network thereby locating a potential carrier unit that is traveling closer to a potential target. As such, this carrier unit could be deemed desirable as a lesser number of hops could potentially be necessary to reach the target, thereby protecting the data from unintentional disclosure, loss or corruption.

At 502, an opportunistic connection can be established. Here, the location and/or motion of a subject device can be considered in determining availability of a transmission opportunistic network. At 504, a determination can be made if a connection is available. If not, establishment of an opportunistic connection continues until the subject unit is within range of an available next-hop device. In an example, data can be stored upon a mobile device that is 'out of range' of any suitable transmission path. As such, data, for example health-related statistics, can continue to be aggregated until the mobile device becomes connected to an appropriate target device. In this example, it can be possible for the mobile device to continually monitor and store physiological statistics of a patient over a period of time. Subsequently, the unit can be automatically configured to forward or dump the data when the device becomes connected to a health care office. These concepts are better illustrated by acts 506 and 508 that follow.

Once an initial connection is made, hop options can be identified as a function of the connected network. For example, as described above, criteria such as relative location and/or motion based upon the origin and target can be factored to determine available hop options. Still further, context such as current activity of a particular unit can be factored into hop option availability.

At 508, a next hop unit can be selected as a function of the dynamic network as well as a function of criteria of each unit within the network. As described above, the next hop can be a function of data type (e.g., voice, health, urgent, confidential, non-urgent) as well as a function of criteria of devices within the network, for example, location, motion, availability, device type, owner, classification, inferred destination, etc. It is to be understood that the examples are too numerous to list thus, alternative aspects that employ features, functions and benefits contemplated herein as well as by those in the art are to be included within the scope of this disclosure and claims appended hereto.

Figure 6:
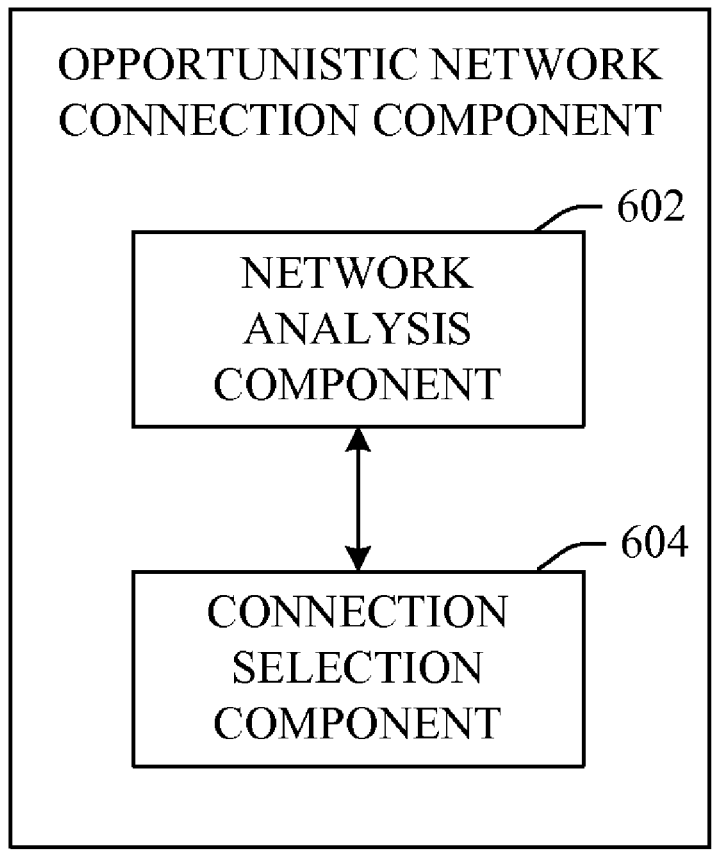
FIG. 6 illustrates an example opportunistic connection component that enables a device to communication with another device in accordance with an aspect of the innovation.

Referring now to FIG. 6, an example block diagram of an opportunistic connection component 102 (as described with reference to FIG. 1) is shown. Generally, an opportunistic connection component 102 can include a network analysis component 602 and a connection selection component 604, each of which will be described in greater detail infra. Together, these components (602, 604) enable a device to intelligently analyze an available network and to thereafter select and appropriate connection in view of those connections available.

The network analysis component 602 can search for an available network or device available for connection. As well, the network analysis component 602 can analyze and/or evaluate the details of available devices within a network. For example, as mentioned above, the network analysis component 602 can search for an available network and subsequently evaluate availability and criteria of devices within the identified network.

The connection selection component 604 can be employed to intelligently decide an appropriate device for which to connect. It is to be understood that the store/forward concepts described herein enable unique opportunities for service providers. For instance, a service provider can offer different rate packages in accordance with reserving a portion of a device's processing capability. In other words, if a user is willing to allow a device to be used as a hop or carrier device for other's traffic, a service provider can incorporate this into the user's service plan, for example, by offering a lower rate if there is an agreement to share resources (e.g., processor, storage). It will be appreciated that these monetization schemes can be based upon most any criteria, for example, permit transfer at a particular time of day, day of week, for a particular type of traffic, from particular origins, etc.

Figure 7:
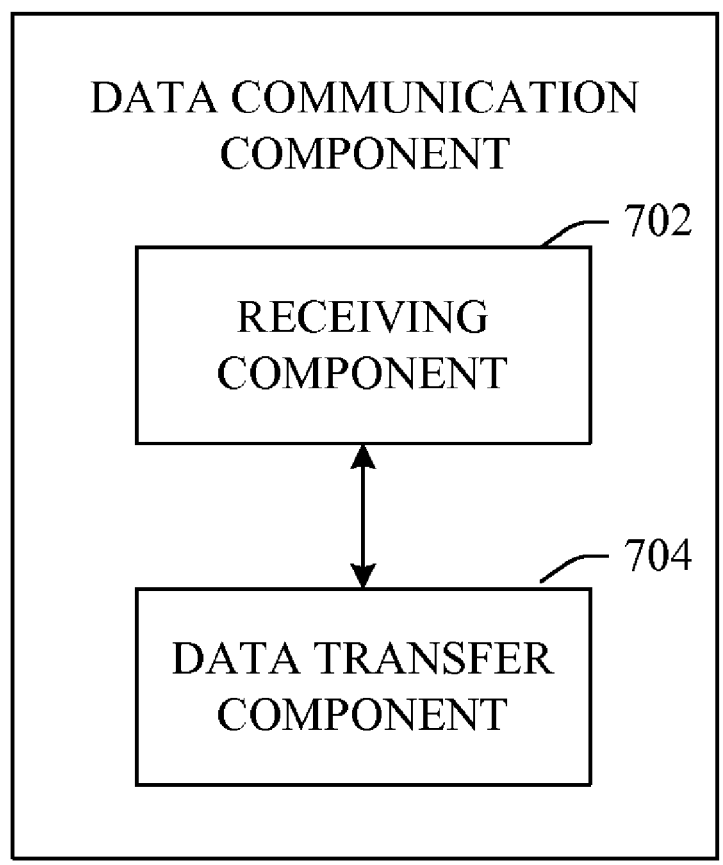
FIG. 7 illustrates an example data communication component that facilitates receipt and transfer of data in accordance with an aspect of the innovation.

FIG. 7 illustrates an example block diagram of a data communication component 104 which generally includes a receiving component 702 and a data transfer component 704. Essentially, the receiving component 702 can receive data from a source (e.g., physiological sensor, environmental sensor, user, application) or group of sources, analyze the data, verify the data and aggregate data (if desired). The data transfer component 704 can effectively forward the data to an appropriate target or group of targets. Each of these components (702, 704) will be described in more detail with reference to the figures that follow.

Figure 8:
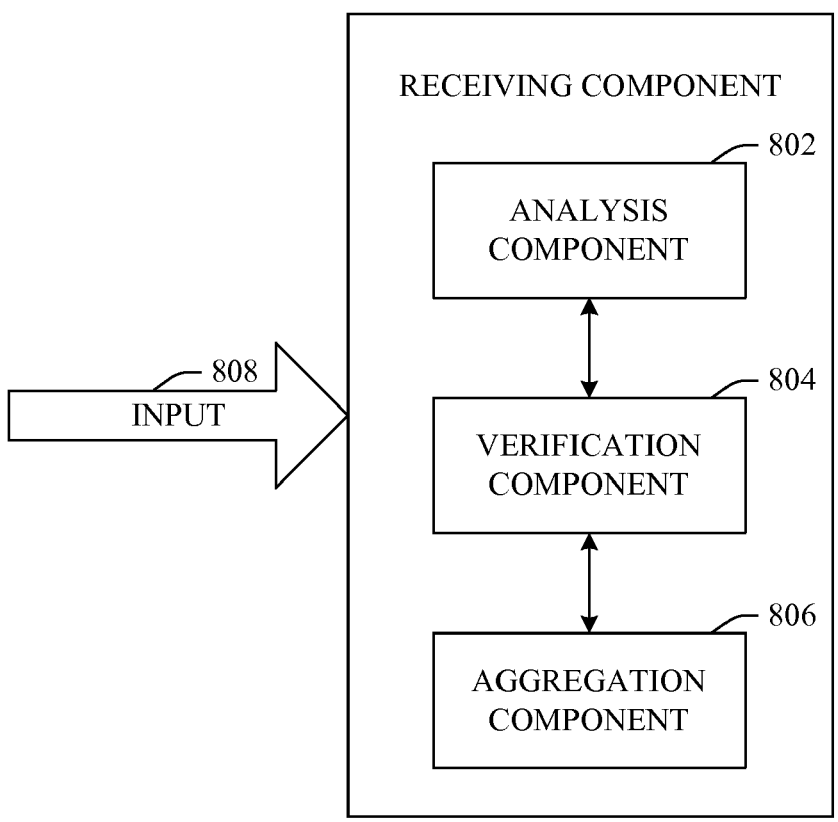
FIG. 8 illustrates an example receiving component that facilitates data analysis, verification and aggregation in accordance with an aspect of the innovation.

FIG. 8 illustrates a block diagram of an example receiving component 702 in accordance with an aspect of the innovation. As shown, generally, the receiving component 702 can include an analysis component 802, a verification component 804 and an aggregation component 806 each of which enable a device to capture information in the 'store' phase of a 'store/forward' process. More particularly, these components (802, 804, 806) enable sophisticated logic with regard to a data input 808, such as health-related data. As will be understood, the input 808 can be of most any data format, including but not limited to, alphanumeric text, audio, video, image, etc.

In operation, the analysis component 802 can evaluate the data to determine criteria of the data, for example, type, size, origin, etc. It is to be appreciated that data can be push to or pulled by way of the receiving component 702. Once analyzed, the receiving component 702 can determine if the data is to be immediately forwarded, aggregated, etc. or if the data should be stored (e.g., cached, buffered) for later action. For example, the receiving component 702, based upon the type of data, can determine if more data is to be received, urgency of delivery (e.g., priority), target location, etc. In addition to core content analysis techniques, the analysis component 802 can also employ techniques such as pattern recognition, speech recognition, or the like to analyze content of the received data.

The verification component 804 can be employed to confirm accurate delivery of the data. Here, accuracy relates both to the lack of corruption as well as completeness of the data. In other words, the verification component 804 can establish if more information is necessary to complete the data transmission before a 'forward' action or transfer of the data is instantiated.

The aggregation component 806 can facilitate collection of additional information if deemed necessary. For example, if the verification component 804 deems a transmission incomplete, the aggregation component 806 can be employed to collect additional information thus, completing the transmission. In addition to completeness, the logic of the verification component 806 can be employed to otherwise determine if more information can be gathered. For example, if it is deemed that current information is to be delivered to a particular target within the network and capacity is still available to capture additional information bound for the same target, in the interest of efficiency, the aggregation component 806 can gather additional information prior to forwarding. For instance, information about a health-related issue can be gathered from other proximate devices in the event that capacity is available. Here, this additional information can give a different perspective of an event such as images of a patient just prior to a heart attack, epileptic seizure, outburst, collapse, etc.

Figure 9:
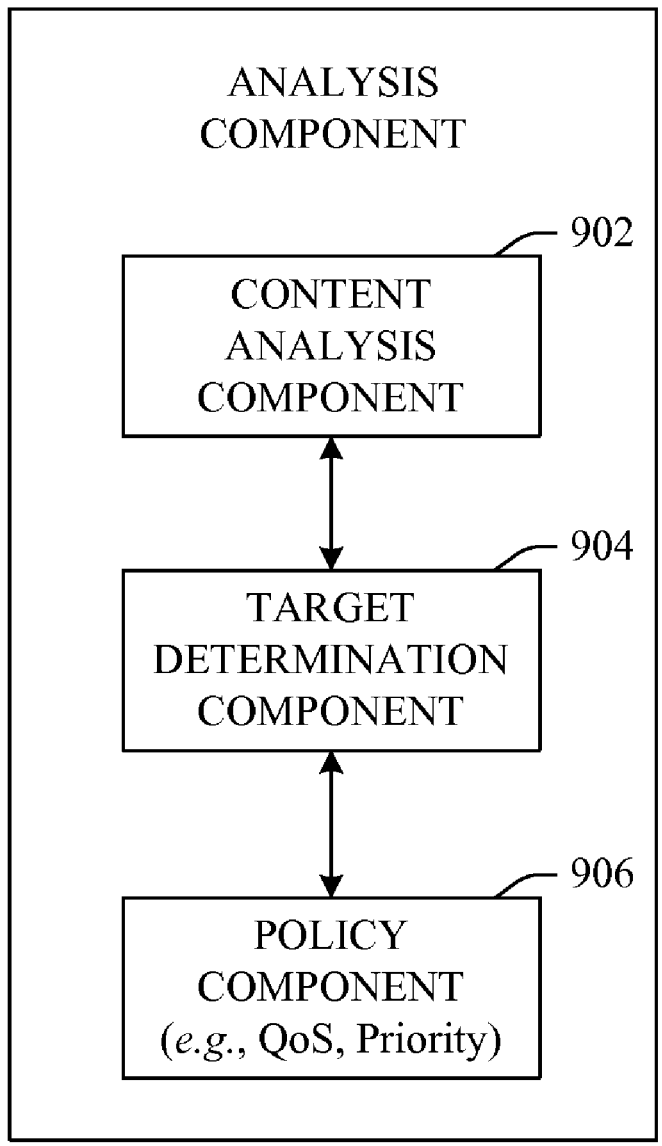
FIG. 9 illustrates an example analysis component that facilitates evaluation of data content in accordance with an aspect of the innovation.

Referring now to FIG. 9, an example block diagram of an analysis component 802 is shown as having a content analysis component 902, a target determination component 904, and a policy component 906. As described above, each of these components contribute to intelligent process of data. Continuing with the health-related example from above, data can be analyzed to determine type and relevance of the data, where the data is to be sent and, based upon determined criteria, how best and most efficiently to transfer the data.

This functionality can be accomplished by the analysis component 902, the target determination component 904 and the policy component 906 respectively.

More specifically, the content analysis component 902 can evaluate received data to determine characteristics that can be used in processing and handling the data. For example, suppose the data is received from a physiological sensor mechanism—in this example, the content analysis can determine what the information represents (e.g., blood pressure measurement from a particular patient) and, based upon the determined content, it can further be determined if the information is urgent, confidential, etc. This determination can be made as a function of policy component 906. Here, the policy component 906 can include rules for quality of service, priority delivery, etc. all of which can be factored to determine delivery.

The target determination component 904 can further employ the policy 906 in determining where to deliver the information. For example, suppose A is a patient of doctor B—here, if it is determined that the information is not urgent, it can routinely be delivered to doctor B no matter how long the delivery may take. However, if it is determined that urgent or priority delivery is desired, the target determination component 904 can identify another suitable target such that action can be promptly taken based upon the type of information. It is also to be understood that, the target determination component can identify multiple targets to which to deliver the information. Continuing with the above example, here, the data can be sent to the alternative location (e.g., emergency medical facility) so as to prompt immediate action while still delivering a copy of the information to doctor B.

Figure 10:
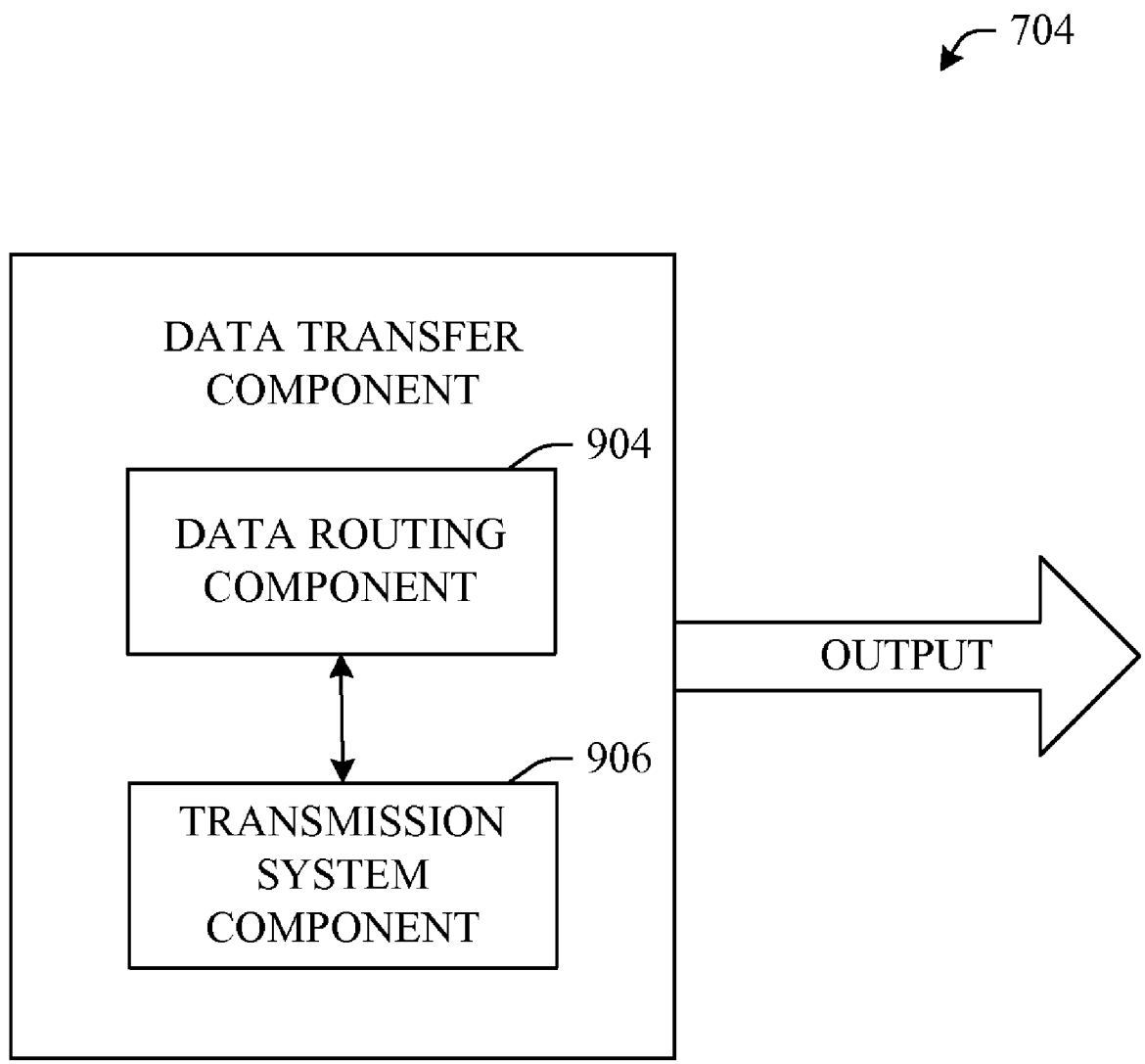
FIG. 10 illustrates an example data transfer component that facilitates routing and transferring of data within an opportunistic network in accordance with an aspect of the innovation.

FIG. 10 illustrates an example block diagram of a data transfer component 704 in accordance with an aspect of the innovation. Generally the data transfer component 704 includes a data routing component 1002 and a transmission system component 1004. As the target destinations are determined by the content analysis component 902, the data routing component 1002 can be employed to determine specifics with regard to transferring the data throughout the network. The data routing component 1002 employs specifics about the data in determining how best to route the data throughout the network.

The transmission system component 1004 enables transfer of the data within the network. For example, the transmission system component 1004 can be based upon a P2P communications network that allows all devices in the network to act as servers and share their files with all other users and devices on the network. In accordance with the opportunistic network described herein, in aspects, most any wireless protocol can be used for example, most any cellular technology, 802.11, infrared, Bluetooth, or the like.

Figure 11:
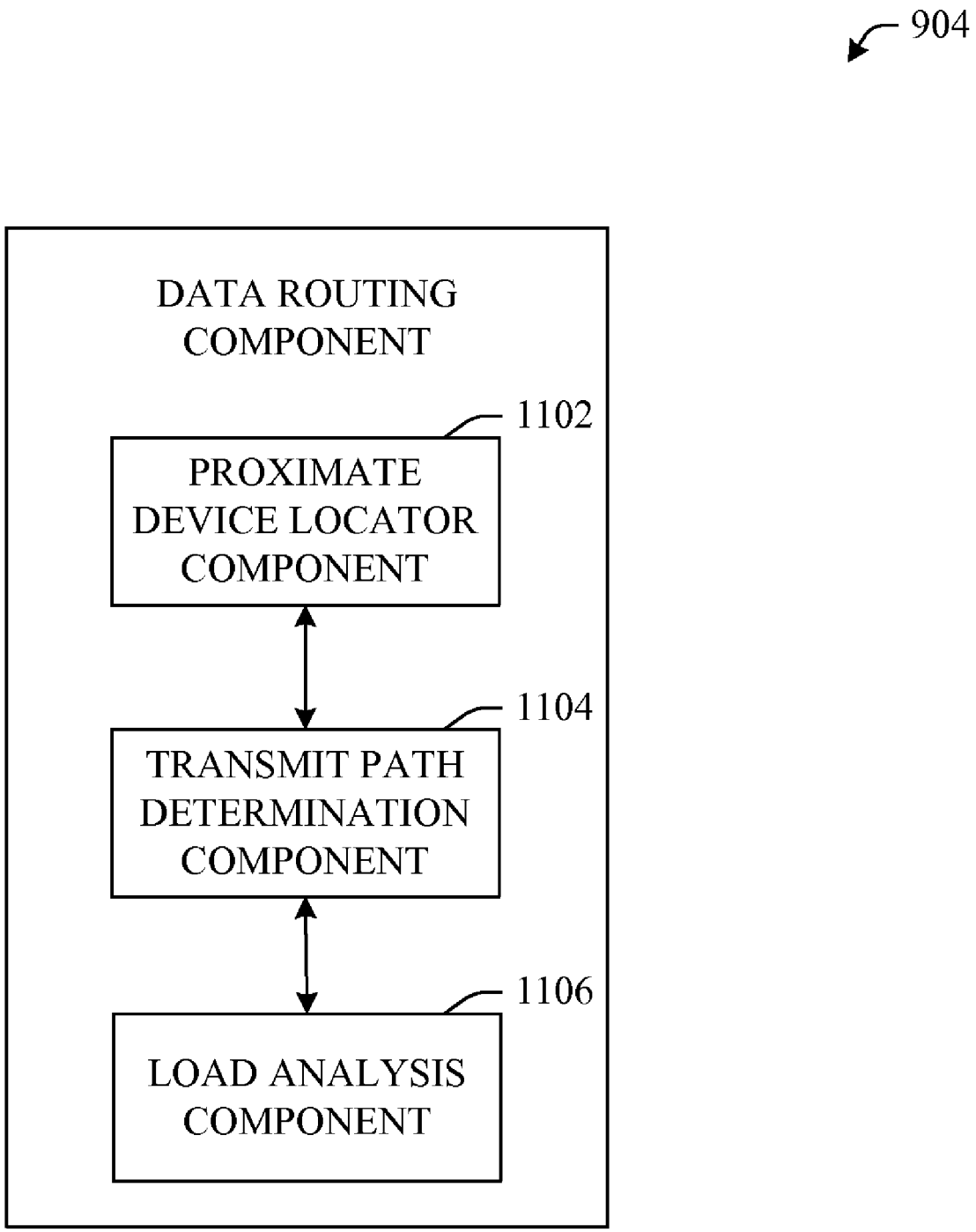
FIG. 11 illustrates an example data routing component that determines available and efficient routes throughout an opportunistic network in accordance with an aspect of the innovation.

FIG. 11 illustrates an example block diagram of a data routing component 904. In determining a route (or group of routes) throughout the opportunistic network, a proximate device locator component 1102 can be used to identify optional 'in-range' devices by which data can be transferred. Further, the proximate device locator component 1102 can include logic capable of inferring locations of devices based upon historical and/or statistical data. In other words, machine learning and reasoning (MLR) mechanisms can be employed to infer if a device will be in range when data is ready or should/could be transferred.

A transmit path determination component 1104 can employ the proximate device information to specify a route (or group of routes) throughout the opportunistic network. This component can also employ MLR mechanisms when determining hops or carrier devices in view of the dynamic network as a function of the data. Both the proximate device locator component 1102 as well as the transit path determination component 1104 can optionally factor device load into decisions. For instance, an optional load analysis component 1106 can be employed to assist in device identification and path determination as a function of current and/or inferred future load of a device.

Figure 12:
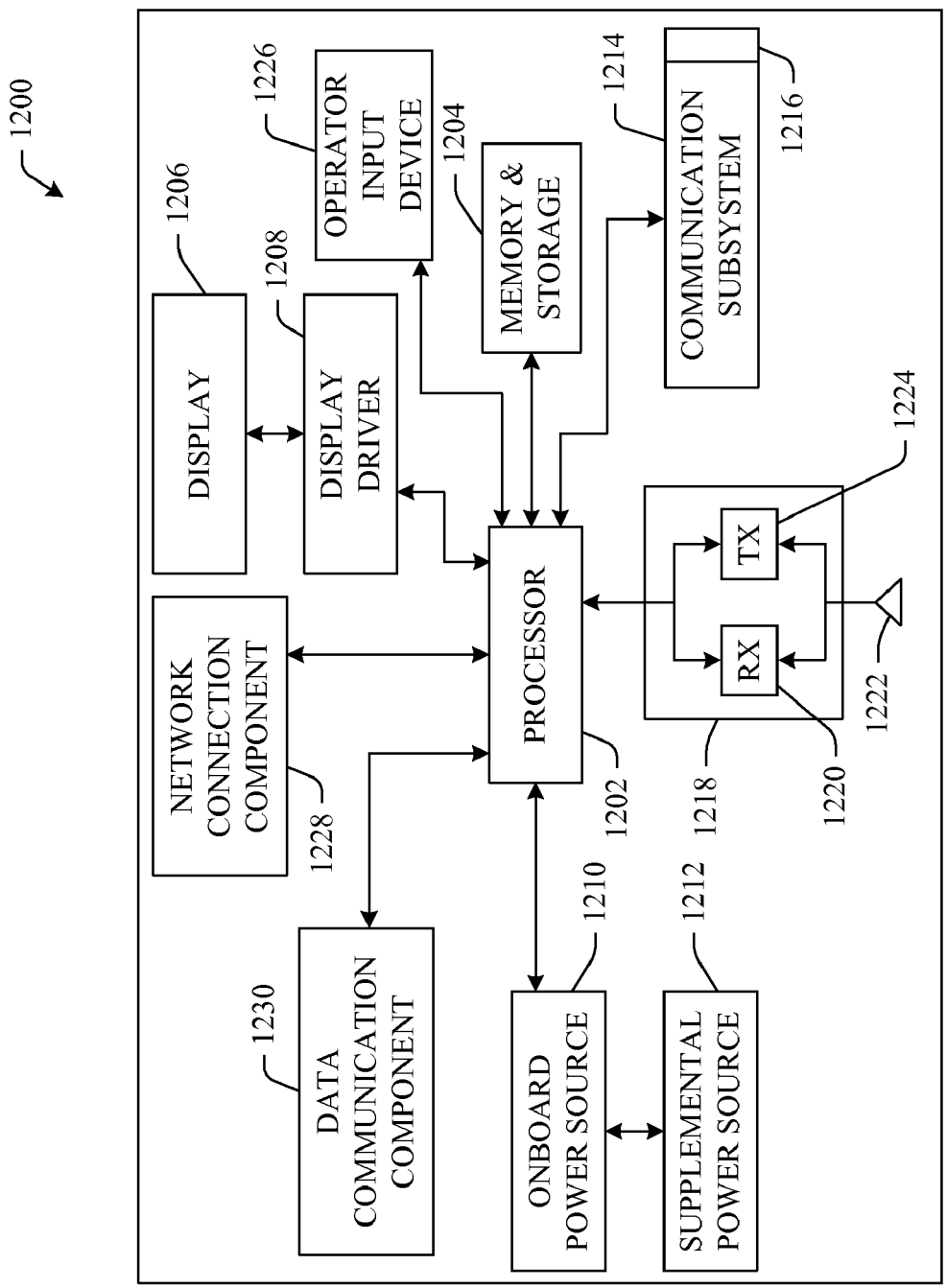
FIG. 12 is a schematic block diagram of a portable device that facilitates analysis and transfer of data (e.g., health-related data) across an opportunistic network according to one aspect of the subject invention.

Referring now to FIG. 12, there is illustrated a schematic block diagram of a portable device 1200 according to one aspect of the subject innovation, in which a processor 1202 is responsible for controlling the general operation of the device 1200. It is to be understood that the portable device 1200 can be representative of most any portable device including, but not limited to, a cell phone, smartphone, PDA, a personal music player, image capture device (e.g., camera), personal game station, health monitoring device, event recorder component, etc.

The processor 1202 can be programmed to control and operate the various components within the device 1200 in order to carry out the various functions described herein. The processor 1202 can be any of a plurality of suitable processors. The manner in which the processor 1202 can be programmed to carry out the functions relating to the subject innovation will be readily apparent to those having ordinary skill in the art based on the description provided herein. As will be described in greater detail infra, an MLR component and/or a rules-based logic component can be used to effect an automatic action of processor 1202.

A memory and storage component 1204 connected to the processor 1202 serves to store program code executed by the processor 1202, and also serves as a storage means for storing information such as data, services, metadata, device states or the like. In aspects, this memory and storage component 1204 can be employed in conjunction with other memory mechanisms that house health-related data. As well, in other aspects, the memory and storage component 1204 can be a stand-alone storage device or otherwise synchronized with a cloud or disparate network based storage means, thereby established a local on-board storage of health-related data.

The memory 1204 can be a non-volatile memory suitably adapted to store at least a complete set of the information that is acquired. Thus, the memory 1204 can include a RAM or flash memory for high-speed access by the processor 1202 and/or a mass storage memory, e.g., a micro drive capable of storing gigabytes of data that comprises text, images, audio, and video content. To this end, it is to be appreciated that the health-related data described herein can be of most any form including text (e.g., sensor readings), images (e.g., captured image sequences) as well as audio or video content. According to one aspect, the memory 1204 has sufficient storage capacity to store multiple sets of information relating to disparate services, and the processor 1202 could include a program for alternating or cycling between various sets of information corresponding to disparate services.

A display 1206 can be coupled to the processor 1202 via a display driver system 1208. The display 1206 can be a color liquid crystal display (LCD), plasma display, touch screen display or the like. In one example, the display 1206 is a touch screen display. The display 1206 functions to present data, graphics, or other information content. Additionally, the display 1206 can display a variety of functions that control the execution of the device 1200. For example, in a touch screen example, the display 1206 can display touch selection buttons which can facilitate a user to interface more easily with the functionalities of the device 1200.

Power can be provided to the processor 1202 and other components forming the device 1200 by an onboard power system 1210 (e.g., a battery pack). In the event that the power system 1210 fails or becomes disconnected from the device 1200, a supplemental power source 1212 can be employed to provide power to the processor 1202 (and other components (e.g., sensors, image capture device)) and to charge the onboard power system 1210. The processor 1202 of the device 1200 can induce a sleep mode to reduce the current draw upon detection of an anticipated power failure.

The device 1200 includes a communication subsystem 1214 having a data communication port 1216, which is employed to interface the processor 1202 with a remote computer, server, service, or the like. The port 1216 can include at least one of Universal Serial Bus (USB) and IEEE 1394 serial communications capabilities. Other technologies can also be included, but are not limited to, for example, infrared communication utilizing an infrared data port, Bluetooth™, etc.

The device 1200 can also include a radio frequency (RF) transceiver section 1218 in operative communication with the processor 1202. The RF section 1218 includes an RF receiver 1220, which receives RF signals from a remote device via an antenna 1222 and can demodulate the signal to obtain digital information modulated therein. The RF section 1218 also includes an RF transmitter 1224 for transmitting information (e.g., data, service) to a remote device, for example, in response to manual user input via a user input 1226 (e.g., a keypad) or automatically in response to a detection of entering and/or anticipation of leaving a communication range or other predetermined and programmed criteria.

An opportunistic connection component 1228 is provided which, as described supra, can facilitate connection of the device 1200 with an opportunistic network which can be used to transmit data in a device-to-device manner (e.g., P2P). Additionally, a data communication component 1230 can be employed to further facilitate delivery of data to a target device via the opportunistic network. It is to be appreciated that these components can enable functionality of like components (and sub-components) described supra.

Figure 13:
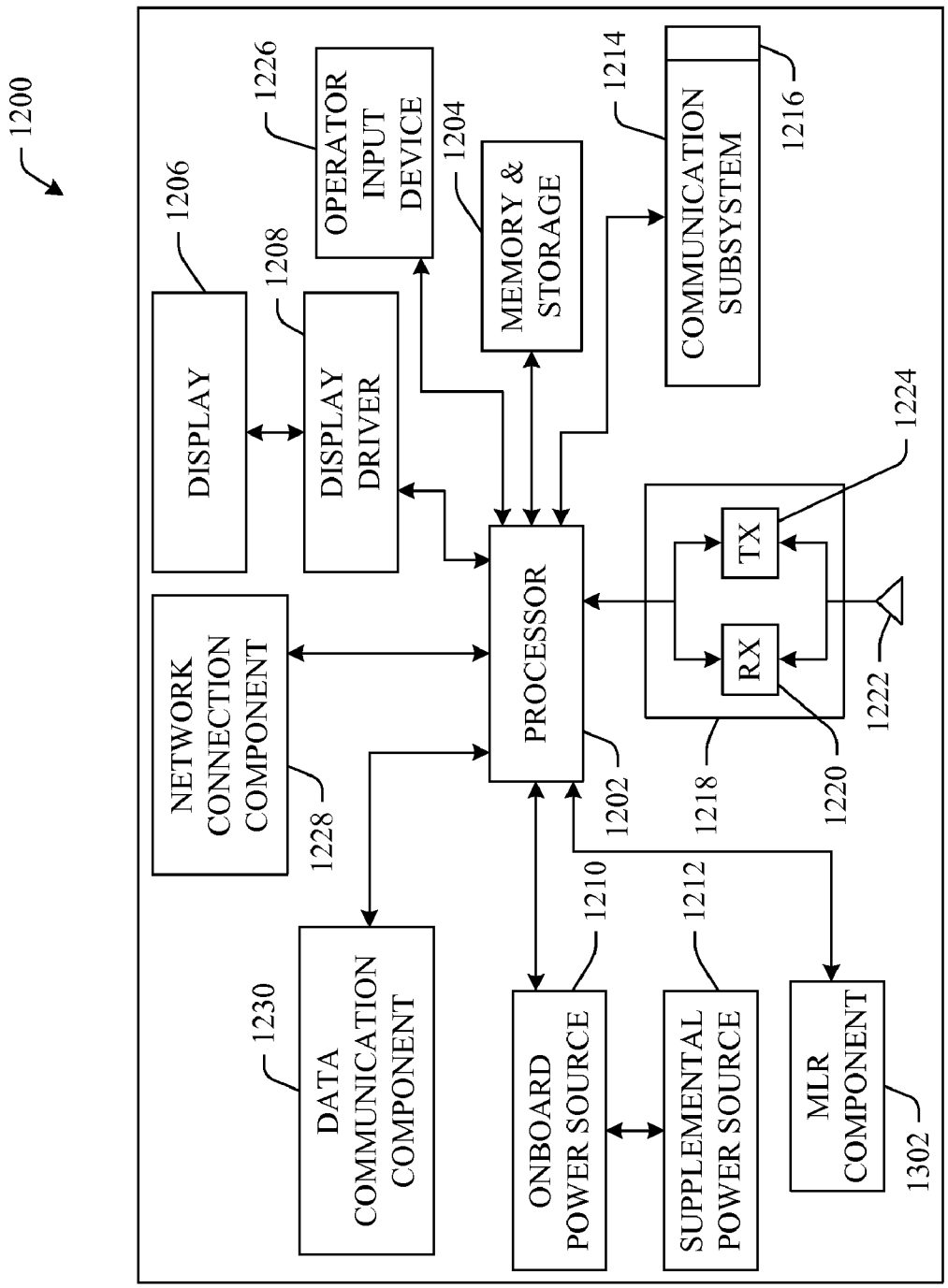
FIG. 13 illustrates an architecture of a portable device that includes a machine learning and reasoning component that can automate functionality in accordance with an aspect of the invention.

FIG. 13 illustrates an example device 1300 that employs MLR component 1302 which facilitates automating one or more features in accordance with the subject innovation. The subject innovation (e.g., in connection with determining carrier devices, delivery priority, data characteristics/completeness) can employ various MLR-based schemes for carrying out various aspects thereof. For example, a process for determining which carrier devices to employ as a function of data type can be facilitated via an automatic classifier system and process. Moreover, where multiple paths to a target are available, the classifier can be employed to determine which carrier devices to select in view of context and other situational factors.

A classifier is a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria how to classify data, where to send data, what priority should be employed, which carrier device(s) to employ, when to store and for how long, when to transmit data, etc. It is further to be appreciated that device 1300 can be equipped with an optional rules-based component (not shown) that facilitates policies and/or threshold based logic to be employed in making determinations associated with the functionality described herein.

In other aspects, the example device 1300 can trade off cost and privacy versus emergency needs. For example, if a user is having a heart attack, it may be a logical tradeoff to reveal confidential information and medical data (e.g., ECG) or how much it costs to send in exchange for reaching help in sufficient time to address the urgency. However, as described supra, in a 'normal' scenario, it can be possible to reduce or limit costs, for example, by storing data until a free network or P2P transfer agent is available rather than use expensive cell-based networks while maintaining data security/privacy.

In another example, the device 1300 can automatically decide (by inference) to send data to a service rather than sending to a node-name. By way of example, an ECG can be sent to a nearby paramedic or doctor, regardless of which one, or sent to whichever device is being carried by the on-call medical resident for Ward B, as opposed to a particular named doctor or named device. As described above, these decisions can be based upon user preference, inference or rule as a function of data content or context.

Still further, implicit trust relationships can be established based upon context. For example, with regard to the privacy and security context, when a device is in a hospital environment, a trust relationship can automatically be established with other devices in near proximity. This automatic trust establishment can facilitate interoperation without restrictive continual authentication demands.

Figure 14:
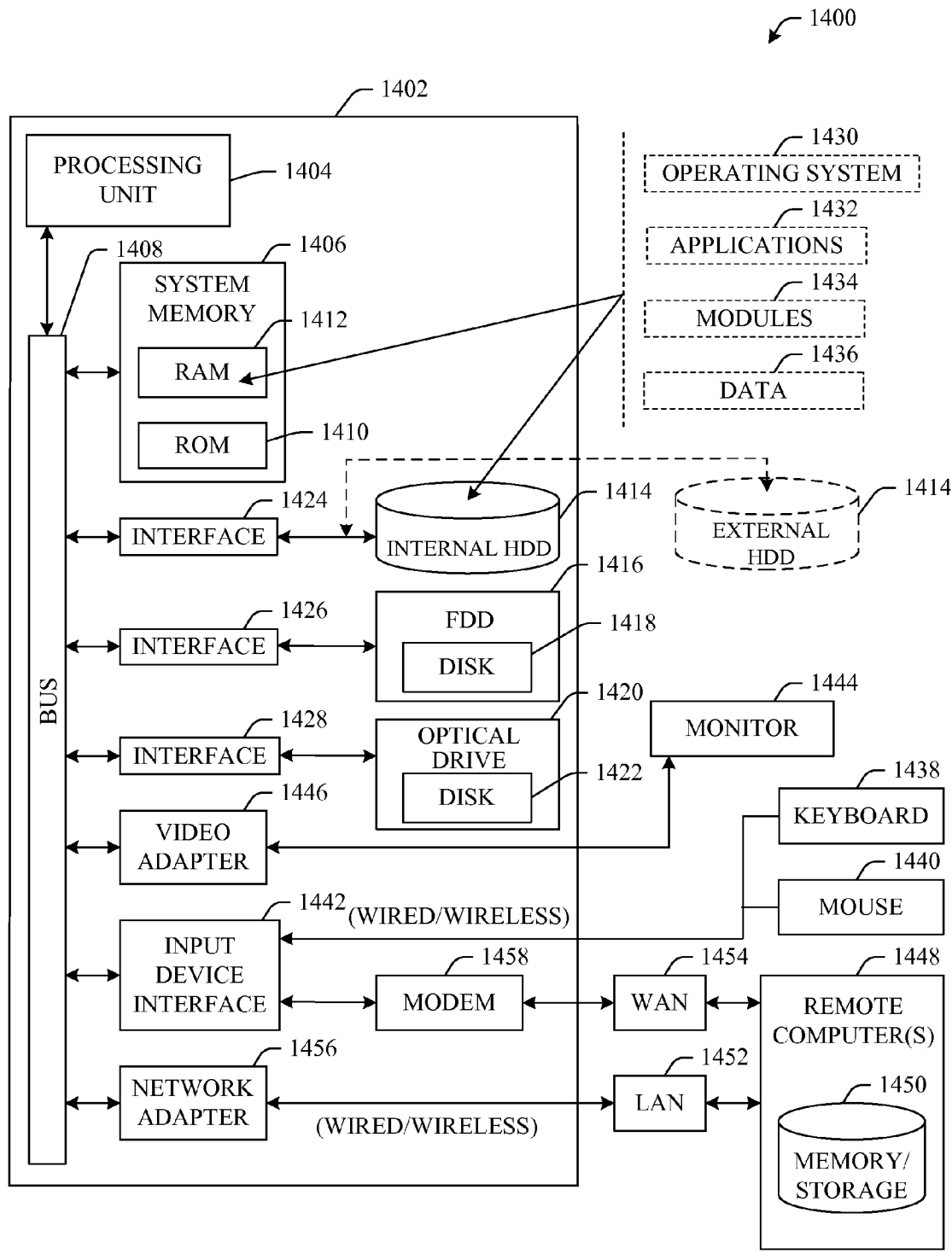
FIG. 14 illustrates a block diagram of a computer operable to execute the disclosed architecture.

Referring now to FIG. 14, there is illustrated a block diagram of a computer operable to execute the disclosed architecture of an opportunistic network-based mobile device and network. In order to provide additional context for various aspects of the subject innovation, FIG. 14 and the following discussion are intended to provide a brief, general description of a suitable computing environment 1400 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 14, the exemplary environment 1400 for implementing various aspects of the innovation includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures may also be employed as the processing unit 1404.

The system bus 1408 can be any of several types of bus structure that may further interconnect to a memory bus (with or without a memory controller), a peripheral bus, and a local bus using any of a variety of commercially available bus architectures. The system memory 1406 includes read-only memory (ROM) 1410 and random access memory (RAM) 1412. A basic input/output system (BIOS) is stored in a non-volatile memory 1410 such as ROM, EPROM, EEPROM, which BIOS contains the basic routines that help to transfer information between elements within the computer 1402, such as during start-up. The RAM 1412 can also include a high-speed RAM such as static RAM for caching data.

The computer 1402 further includes an internal hard disk drive (HDD) 1414 (e.g., EIDE, SATA), which internal hard disk drive 1414 may also be configured for external use in a suitable chassis (not shown), a magnetic floppy disk drive (FDD) 1416, (e.g., to read from or write to a removable diskette 1418) and an optical disk drive 1420, (e.g., reading a CD-ROM disk 1422 or, to read from or write to other high capacity optical media such as the DVD). The hard disk drive 1414, magnetic disk drive 1416 and optical disk drive 1420 can be connected to the system bus 1408 by a hard disk drive interface 1424, a magnetic disk drive interface 1426 and an optical drive interface 1428, respectively. The interface 1424 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1402, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. It is appreciated that the innovation can be implemented with various commercially available operating systems or combinations of operating systems.

A user can enter commands and information into the computer 1402 through one or more wired/wireless input devices, e.g., a keyboard 1438 and a pointing device, such as a mouse 1440. Other input devices (not shown) may include a microphone, an IR remote control, a joystick, a game pad, a stylus pen, touch screen, or the like. These and other input devices are often connected to the processing unit 1404 through an input device interface 1442 that is coupled to the system bus 1408, but can be connected by other interfaces, such as a parallel port, an IEEE 1394 serial port, a game port, a USB port, an IR interface, etc.

A monitor 1444 or other type of display device is also connected to the system bus 1408 via an interface, such as a video adapter 1446. In addition to the monitor 1444, a computer typically includes other peripheral output devices (not shown), such as speakers, printers, etc.

The computer 1402 may operate in a networked environment using logical connections via wired and/or wireless communications to one or more remote computers, such as a remote computer(s) 1448. The remote computer(s) 1448 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1450 is illustrated. The logical connections depicted include wired/wireless connectivity to a local area network (LAN) 1452 and/or larger networks, e.g., a wide area network (WAN) 1454. Such LAN and WAN networking environments are commonplace in offices and companies, and facilitate enterprise-wide computer networks, such as intranets, all of which may connect to a global communications network, e.g., the Internet.

When used in a LAN networking environment, the computer 1402 is connected to the local network 1452 through a wired and/or wireless communication network interface or adapter 1456. The adapter 1456 may facilitate wired or wireless communication to the LAN 1452, which may also include a wireless access point disposed thereon for communicating with the wireless adapter 1456.

When used in a WAN networking environment, the computer 1402 can include a modem 1458, or is connected to a communications server on the WAN 1454, or has other means for establishing communications over the WAN 1454, such as by way of the Internet. The modem 1458, which can be internal or external and a wired or wireless device, is connected to the system bus 1408 via the serial port interface 1442. In a networked environment, program modules depicted relative to the computer 1402, or portions thereof, can be stored in the remote memory/storage device 1450. It will be appreciated that the network connections shown are exemplary and other means of establishing a communications link between the computers can be used.

The computer 1402 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 15:
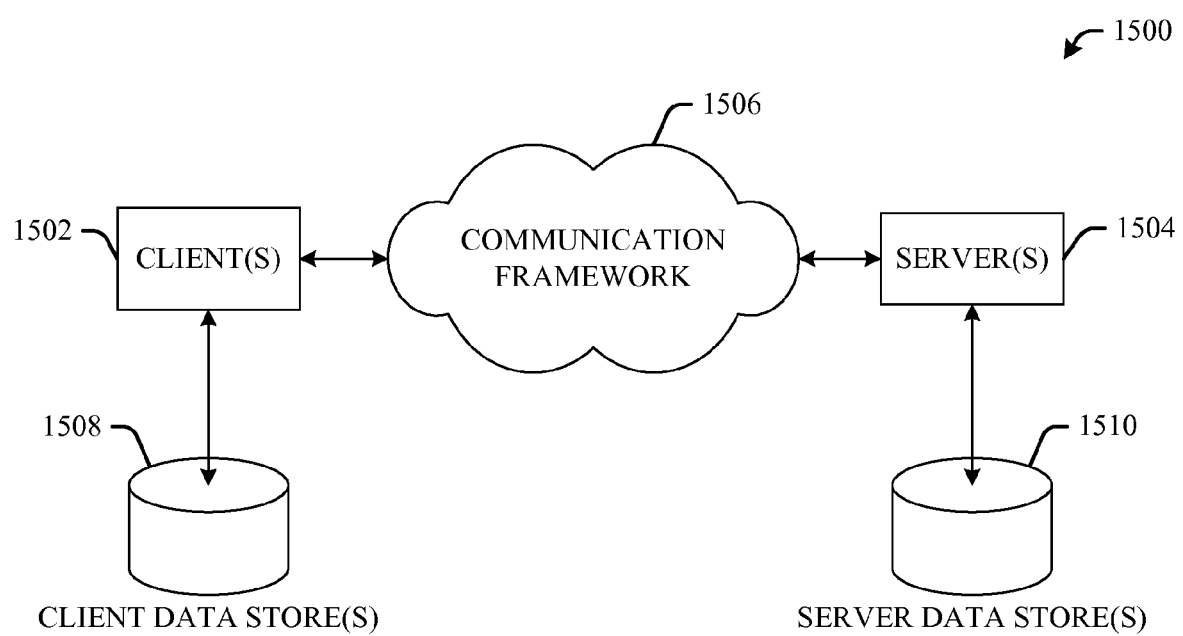
FIG. 15 illustrates a schematic block diagram of an exemplary computing environment in accordance with the subject innovation.

Referring now to FIG. 15, there is illustrated a schematic block diagram of an exemplary computing environment 1500 in accordance with the subject wireless opportunistic network and/or device innovation. The system 1500 includes one or more client(s) 1502. The client(s) 1502 can be hardware and/or software (e.g., threads, processes, computing devices). The client(s) 1502 can house cookie(s) and/or associated contextual information by employing the innovation, for example.

The system 1500 also includes one or more server(s) 1504. The server(s) 1504 can also be hardware and/or software (e.g., threads, processes, computing devices). The servers 1504 can house threads to perform transformations by employing the innovation, for example. One possible communication between a client 1502 and a server 1504 can be in the form of a data packet adapted to be transmitted between two or more computer processes. The data packet may include a cookie and/or associated contextual information, for example. The system 1500 includes a communication framework 1506 (e.g., a global communication network such as the Internet) that can be employed to facilitate communications between the client(s) 1502 and the server(s) 1504.

Communications can be facilitated via a wired (including optical fiber) and/or wireless technology. The client(s) 1502 are operatively connected to one or more client data store(s) 1508 that can be employed to store information local to the client(s) 1502 (e.g., cookie(s) and/or associated contextual information). Similarly, the server(s) 1504 are operatively connected to one or more server data store(s) 1510 that can be employed to store information local to the servers 1504.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method comprising:
   establishing an opportunistic networking infrastructure by occasional or periodic interconnection of a plurality of mobile devices;
   receiving data at an origin device to be delivered to a target entity on a mobile device;
   aggregating the data on the origin device;
   determining whether capacity is still available to capture additional information bound for the target entity;
   upon determining that capacity is still available, capturing, on the origin device, additional information from at least one other proximate device;
   determining priority of transmission based on an analysis of a content of the data;
   identifying a communication path through the opportunistic networking infrastructure as a function of the priority; and
   based on an occurrence of an opportunity to transmit the data, transferring the data and the additional information to the target entity by way of the communication path.

2. The method of claim 1, the establishing an opportunistic networking infrastructure including establishing at least one peer-to-peer connection.

3. The method of claim 1, the establishing an opportunistic networking infrastructure including establishing hybrid connections including at least one peer-to-peer connection and at least one hub-and-spoke network connection.

4. The method of claim 1, the identifying the communication path including identifying a next hop toward the target entity based on criteria including at least one of a location, a time of day, traffic or a sender identity.

5. The method of claim 1, further comprising:
   determining whether the aggregated data is complete for transmission; and
   upon determining that the aggregated data is not complete for transmission, collecting additional information to complete the aggregated data for transmission.

6. The method of claim 1, further comprising determining an alternative entity to the target entity to which to transfer the data and additional information, based at least partly on the priority.

7. A computer storage medium that is not a signal storing instructions, the instructions in response to execution by one or more computing devices implementing the method of claim 1.

8. A mobile communication device comprising at least one processor programmed to carry out the method of claim 1.

9. A method comprising:
   aggregating data on a communication device via at least one connection of an opportunistic network;
   determining whether additional data capacity is available on the communication device;
   based on determining that additional data capacity is available on the communication device, collecting additional information on the communication device via at least one other connection of the opportunistic network; and
   based upon occurrence of an opportunity to establish a connection within the opportunistic network to a target device, transmitting the aggregated data and additional information to the target device.

10. The method of claim 9, the transmitting the aggregated data and additional information comprising identifying a path to the target device through the opportunistic network.

11. The method of claim 10, the identifying the path comprising selecting a next hop unit in the opportunistic network to which transfer the aggregated data and additional information.

12. The method of claim 11, the selecting the next hop unit comprising analyzing criteria including at least one of a location or motion of the communication device relative to the target device.

13. A computer storage medium that is not a signal storing instructions, the instructions in response to execution by one or more computing devices implementing the method of claim 9.

14. A mobile communication device comprising at least one processor programmed to carry out the method of claim 9.

15. A portable communication device comprising:
   a processor; and
   a memory coupled to the processor and storing instructions executable by the processor to implement functional components including
      an opportunistic network connection component configured to facilitate participation of the portable communication device in an opportunistic communication infrastructure, and
      a receiving component configured to
         aggregate information from a first participating device of the opportunistic communication infrastructure for transfer to a target device,
         determine whether capacity is available to capture additional information to be transferred to the target device, and
         based on determining that capacity is available, capture the additional information from a second participating device of the opportunistic communication infrastructure prior to transferring the aggregated information and the additional information to the target device.

16. The portable communication device of claim 15, the receiving component comprising an analysis component configured to evaluate a content of at least one of the aggregated or additional information.

17. The portable communication device of claim 16, the analysis component comprising a target determination component configured to identify the target device based at least partly on the content of the at least one of the aggregated or additional information.

18. The portable communication device of claim 17, further comprising a proximate device locator component configured to identify an in-range device by which information can be transferred.

19. The portable communication device of claim 18, further comprising a transmit path determination component configured to employ proximate device information to specify at least one route through the opportunistic communication infrastructure to the target device.

20. The portable communication device of claim 16, the analysis component comprising a policy component configured to apply rules associated with characteristics of the content of the aggregated or additional information to determine the target device.

* * * * *